United States Patent
Daikuzono

(10) Patent No.: US 6,224,590 B1
(45) Date of Patent: *May 1, 2001

(54) LASER BALLOON CATHETER

(75) Inventor: Norio Daikuzono, Chiba-ken (JP)

(73) Assignee: S.L.T. Japan Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/551,395

(22) Filed: Nov. 1, 1995

Related U.S. Application Data

(63) Continuation of application No. 08/131,635, filed on Oct. 5, 1993.

(51) Int. Cl.[7] ............................................. A61B 18/18
(52) U.S. Cl. ........................... 606/15; 606/10; 606/17
(58) Field of Search ............................................. 606/2–19

(56) References Cited

U.S. PATENT DOCUMENTS

| | | |
|---|---|---|
| 4,445,892 * | 5/1984 | Hussein et al. ............... 604/101.05 |
| 4,512,762 | 4/1985 | Spears . |
| 4,799,479 | 1/1989 | Spears . |
| 4,878,492 | 11/1989 | Sinofsky et al. . |
| 4,913,142 * | 4/1990 | Kittrell et al. ............................ 606/7 |
| 5,370,608 * | 12/1994 | Sahota et al. ............................ 606/17 |
| 5,415,654 * | 5/1995 | Daikuzono ............................... 606/7 |

FOREIGN PATENT DOCUMENTS

| | | | |
|---|---|---|---|
| 9210142 * | 6/1992 | (WO) | ................................... 606/15 |

* cited by examiner

Primary Examiner—David M. Shay
(74) Attorney, Agent, or Firm—McDermott, Will & Emery

(57) ABSTRACT

A laser balloon catheter for emitting in a balloon, laser lights which are transmitted through optical fibers and for irradiating the tissue with the laser lights transmitted through the balloon comprises laser light emitting means having a laser light emitting end of said optical fibers or a laser light transmittable member provided at the emitting end of the optical fibers which receives the laser lights to emit them, a first inflatable balloon provided around said light emitting means for transmitting the laser lights from said emitting means toward the tissue, a first fluid passage for supplying fluid into said first balloon to inflate the same and for discharging the fluid therefrom to deflate the same, a second inflatable balloon provided in front of said first balloon, a second fluid passage for supplying the fluid into said second balloon to inflate the same and for discharging the fluid therefrom to deflate the same.

13 Claims, 7 Drawing Sheets

DISTANCE FROM WALLS OF THE URETHRA

LASER BALLOON CATHETER

This application is a continuation of application Ser. No. 08/131,635 filed Oct. 5, 1993.

DETAILED DESCRIPTION OF THE INVENTION

1. Field of the Invention

The present invention relates to a laser balloon catheter which is inserted into the body cavities such as the gullet, the stomach and the prostate for the laser treatment thereof.

2. Prior Art

Laser balloon catheters are used for opening the clogged portions of the blood vessels. Hyperthermia treatment using the laser balloon catheters for irradiating the cancer tissues with laser lights are conducted.

The structure of such type of the laser balloon catheters is disclosed, for example, in U.S. Pat. No. 4,512,762. In this U.S. Patent, a lumen tube surrounding optical fibers is provided and a balloon is provided at the front end of the optical fibers to surround the front end thereof.

Another structure of the catheter in which a balloon is provided with an acoustic sensor for controlling the vaporization of the tissue is disclosed in U.S. Pat. No. 4,799,479.

A catheter in which a tube member is provided at the front end of a balloon and liquid is caused to flow through a through-hole formed on the tube member is disclosed in U.S. Pat. No. 4,878,492.

However, the laser balloon catheter having only one balloon may be unwantedly removed from the urethra or shifted while the catheter is manipulated. Even if the balloon is preliminarily set in the prostate, shifting of the balloon toward the entrance of the urethra may cause the sphincter muscle to be irradiated with laser lights, resulting in thermal damage to the sphincter muscle.

SUMMARY OF THE INVENTION

It is, therefore, an object of the present invention to provide a laser balloon catheter which can be set in position, and thus is capable of irradiating only a desired portion of the prostate with laser lights and of preventing the sphincter muscle from being damaged due to removal of the catheter from the urethra and shifting of the catheter toward the entrance of the urethra.

It is another object of the present invention to provide a laser balloon catheter which can discharge urine externally through the catheter when urination occurs during treatment.

In order to overcome the above mentioned problems, the present invention provides a laser balloon catheter for emitting in a balloon, laser lights which are transmitted through optical fibers and for irradiating the tissue with the laser lights transmitted through the balloon, comprising laser light emitting means having a laser light emitting end of said optical fibers or a laser light transmittable member provided at the emitting end of the optical fibers which receives the laser lights to emit them; a first inflatable balloon provided around said light emitting means for transmitting the laser lights from said emitting means toward the tissue; a first fluid passage for supplying fluid into said first balloon to inflate the same and for discharging the fluid therefrom to deflate the same; a second inflatable balloon provided in front of said first balloon; and a second fluid passage for supplying the fluid into said second balloon to inflate the same and for discharging the fluid therefrom to deflate the same.

After the laser balloon catheter has been inserted into, for example, the urethra, the first balloon is inflated by supplying thereto, fluid preferably cooling water and similarly, the second balloon is inflated by supplying fluid, preferably cooling water thereto.

The laser lights emitted from the laser light emitting means comprising the emitting end of the optical fibers or a laser light transmittable member provided at the emitting end of the fibers are impinged on a target tissue, for example, the prostate via a first balloon. This causes the prostate to be warmed or heated up to a temperature at which the tissue necroses. Then the prostate will be recovered soon after the operation.

Since the second balloon is provided in front of the first balloon in the present invention, the neck portion between the first and second balloon is positioned between the neck of the bladder so that the laser balloon catheter is engaged with the neck portion of the bladder to prevent the laser balloon catheter from removing from the bladder during the operation. Urine can be discharged through the second balloon located in the bladder.

In contrast to this, if only one balloon is used, the laser balloon catheter may be removed from the urethra or may be shifted in position during the manipulation of the catheter. Since it is necessary to avoid the thermal damage on the position other than the prostate, particularly the sphincter muscle portion, the length of the balloon is preliminarily determined in consideration of the length of the prostate. If the balloon is shifted in position toward the entrance of the urethra after positioning of the balloon portion of the prostate, the sphincter muscle portion may be irradiated with laser lights, resulting in thermal damage to the sphincter muscle.

Since positioning of the laser balloon catheter so that the neck portion between the first and second balloons abuts on the neck portion of the bladder will prevent the laser balloon catheter from moving. This positively prevents the thermal damage of the sphincter muscle.

Since the optical fibers can be easily broken by the application of an excessive force thereto, it is effective to provide guide means which surrounds the optical fibers to protect the optical fibers. A space within the guide means may be used as a communication passage for fluid used for inflating the first balloon.

Connecting means is provided in front of the laser light emitting means. The connecting means is linked with said guide means by the laser light transmittable and flexible linking means to secure the front end side of the first balloon to said connecting means. This provides a structure enabling the first balloon to be inflated or deflated. An inserting force can be applied to even the connecting means by the linking means to enable the present catheter to be smoothly inserted into the position of a target tissue.

The guide means can be made a coaxial double structure. A space between the first and second guide means may be used as a first fluid passage for inflating the first balloon by providing the first guide means to surround the optical fibers and by providing the second guide means around the periphery of the first guide means. The base end portion of the first balloon can be secured to said second guide means. Said connecting means can be used as means for securing the second balloon.

In accordance with the present invention, there is further provided a laser balloon catheter for emitting in a balloon laser lights which are transmitted through optical fibers and for irradiating the tissue with the laser lights transmitted through the balloon, comprising laser light emitting means having a laser light emitting end of said optical fibers or a laser light transmittable member provided at the emitting end of the optical fibers which receives the laser lights to emit them; a first inflatable balloon provided around said light emitting means for transmitting the laser lights from said emitting means toward the tissue; a first fluid passage for supplying fluid into said first balloon to inflate the same and for discharging the fluid therefrom to deflate the same; a second inflatable balloon provided in front of said first balloon; a second fluid passage for supplying the fluid into said second balloon to inflate the same and for discharging the fluid therefrom to deflate the same; connecting means disposed in front of said laser emitting means; a first flexible and laser light transmittable linking means for linking said connecting means with said guide means; plug means disposed in front of said connecting means; and second linking means for linking said plug means with said connecting means; said front end of said first balloon being secured to said connecting means; the second balloon being secured to said plug means and said connecting means at the front and base ends thereof, respectively.

When the laser balloon catheter is inserted into the urethra and the bladder, an inserting force from the first guide means which surrounds the optical fibers and the second guide means surround the first guide means is smoothly transmitted to the linking means, the connecting means, the second linking means and then the plug means. Thus, insertion is smoothly conducted. Since the first linking means is made of a laser light transmittable material, the laser lights are transmitted through the first linking means and are incident upon the target tissue via the first balloon.

The first linking means is preferably tubular in shape and the wall of the first linking means is formed with a communicating hole. Accordingly, the second guide means is provided around the first guide means. Fluid, for example, water is continuously supplied to a space between the first and second guide for inflating the first balloon. Part of the fluid is introduced to the linking means from said communicating hole and is returned to the first guide means to be discharged for continuously cooling a space within the first balloon. The flow of water can be reversed.

Said plug means is formed with a through-hole extending therethrough. It is preferable that the through-hole opens at one end thereof and is communicated with a discharging passage leading to the outside of the catheter. When urination occurs in treatment, urine can be externally discharged via said through-hole and urination passage.

The urination passage for the urine may extend through the first balloon and a space between the first and second guide means.

DESCRIPTION OF PREFERRED EMBODIMENTS

Figure 1:
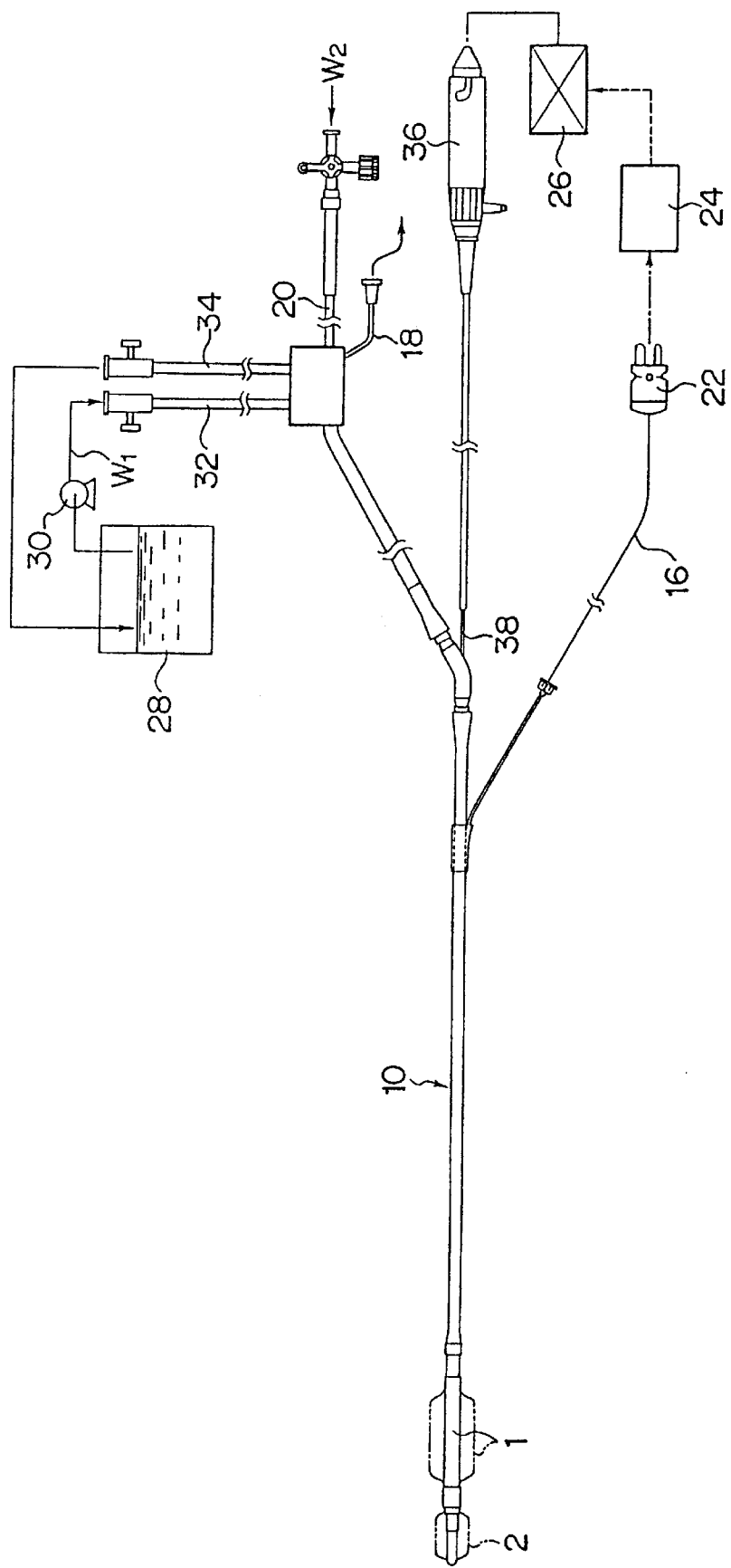
FIG. 1 is a view showing the whole of the laser light irradiation system of the present invention.

Now, the present invention will become more apparent from the description of the preferred embodiments illustrated in the drawings.

FIG. 1 shows the whole of a laser balloon catheter system, which is provided with first and second balloons 1 and 2 at the front end thereof. An-insertion guide 10 has an inner first guide 12 and a second guide 14 which surrounds the first guide 12. A lead line 16 for a temperature sensor, a urination tube 18 and a second balloon inflating coolant supply line 20 are provided between first and second guides 12 and 14. The lead line 16 for the temperature sensor is connected to a connector 22. A signal representative of the temperature is input to a temperature control unit 24 via the connector 22 for driving a laser light generator 26. Urine is discharged via the urination tube 18 when urination occurs during treatment. For example, water W2 is supplied to the second balloon inflating coolant supply tube line 22.

After fluid for inflating the first balloon 1, for example, water W1 is supplied to a tube 32 from a cooling water tank 28 by means of a circulating pump 30, it flows through a space between the first and second guides 12 and 14 and is used for inflating the first balloon 1 and thereafter flows into the first guide 12 and is returned to the cooling water tank 28. The water in the cooling water tank 28 is adjusted to a given temperature.

Laser lights, preferably Nd-YAG laser lights, from the laser light generator 26 are transmitted through the connector 36 and the optical fiber 38.

Figure 2:
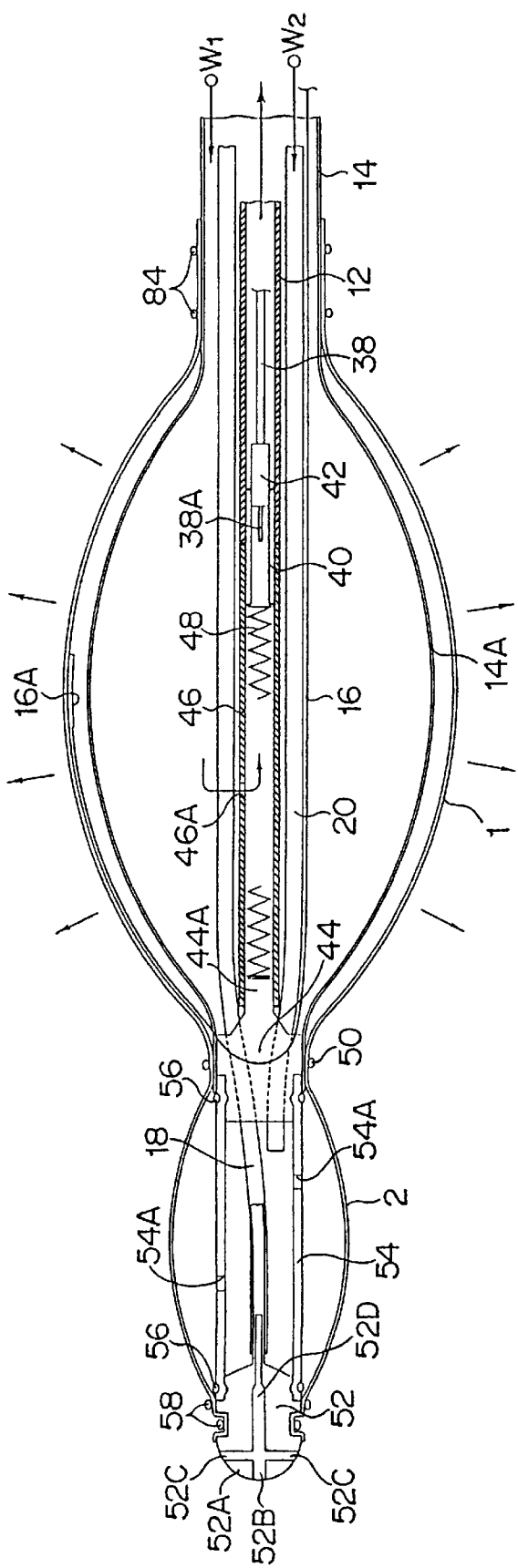
FIG. 2 is a longitudinal sectional view showing the structure of the front end portion of a laser balloon catheter.

The structure of the front end portion of the laser balloon catheter is illustrated in FIG. 2. That is, the optical fiber 38 is provided within the first guide 12 comprising a plastic tube made of polyethylene and the like. A heat resistive protection tube 40 having a high rigidity is provided within the front end portion of the first guide 12. A holder 42 made of metal is disposed within the protection tube 40 for holding the front end of the optical fiber 38.

Figure 3:
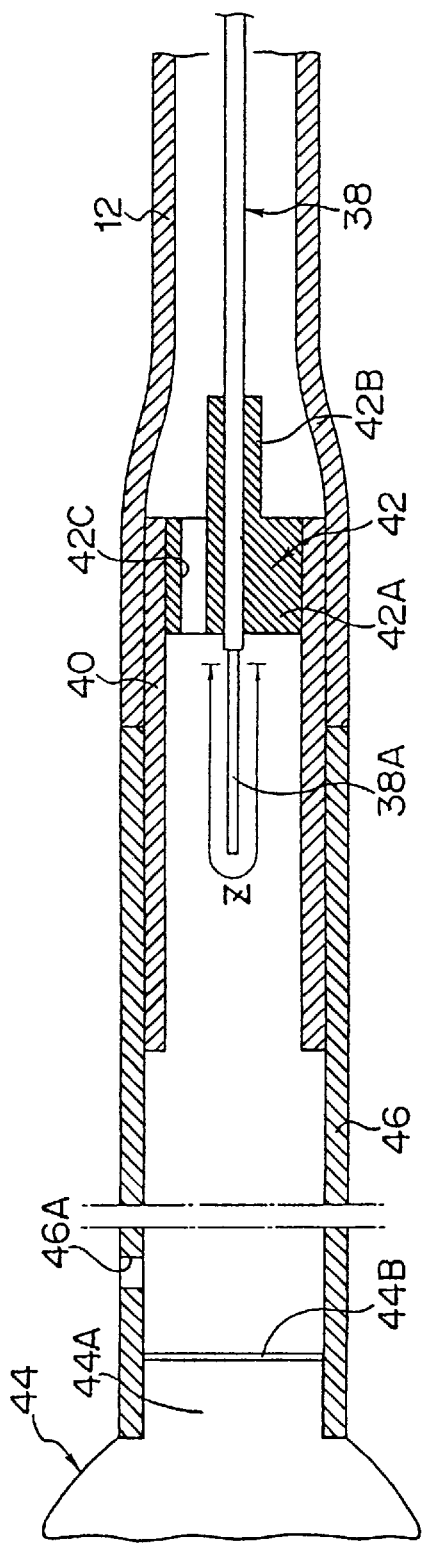
FIG. 3 is an enlarged longitudinal sectional view showing the main part of the front end portion of the catheter.
Figure 4:
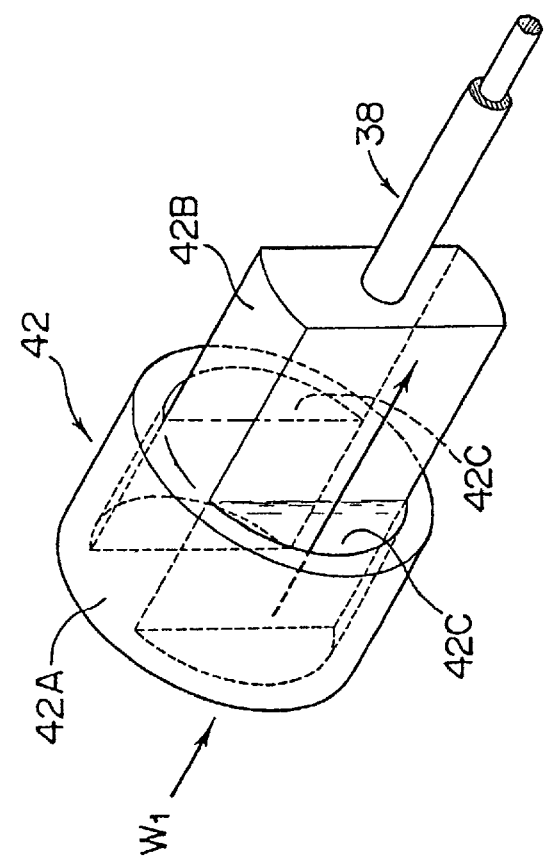
FIG. 4 is a schematic view of a holder.

The manner of holding the optical fiber 38 is illustrated in FIGS. 3 and 4. That is, the holder 42 has a circular portion 42A on the front end side and a flat holding portion 42B on the rear end side. The circular portion 42 is formed with through-holes 42C on both sides thereof. The holder 42 is plated with reflective metal, such as gold for reflecting laser lights. The optical fiber 38 passes through the holding portion 42B and the circular portion 42A. The optical fiber 38 extending beyond the front end of the circular portion 42A has no clad so that a core 38A of the fiber 38 is exposed. Accordingly, laser lights are emitted from the core portion 38A. The laser lights are emitted from the front end of the core 38 at a higher percentage in this case. In order to emit the laser lights from the sides of the core at a higher rate, working to provide the core with rough surface, coating of a film including a light scattering material or coating of a film including light absorbing powders such as carbon for converting optical energy into the thermal energy is conducted over the area Z in FIG. 3.

A connector 44 is provided at the laser emitting end which is a front portion extending beyond the front end of the optical fiber. The connector 44 has a diameter reduced portion 44A at the rear end thereof, a first linking tube 46 made of plastics through which laser lights are transmittable is provided straddling the periphery of the diameter reduced portion 44A and the protection tube 40. The first linking tube 46 is disposed on the outer surface of the protection tube 40 in such a manner that it abuts upon the front end of the first guide 12. The first linking tube 46 is formed with a communicating hole 46A on an appropriate position. A coil spring 48 is provided within the first linking tube 46 between the rear end of the diameter reduced portion 44A and the front end of the protection tube 40. The coil spring 48 is plated with a laser light reflective film such as gold on the outer surface thereof. The diameter reduced portion 44A is coated with a laser light reflective film, such as gold coating layer 44B on the rear end surface thereof. In a preferred embodiment of the present invention, the laser lights are scattered on the inner surfaces of the first linking tube 46 and the protection tube 40. An approach to scatter the laser light may include working of the inner surfaces of the first linking tube 46 and the protection tube 40 into rough surfaces and depositing powders of alumina or silica on the inner surface by baking.

The second guide 14 is formed of a flexible plastic material such as ethylene vinyl acetate or polyethylene and has a preliminarily inflated portion 14A at the front end thereof. The front end portion of the second guide 14 surrounds the periphery of the connector 44 and is secured 14 together with the first balloon 1 by being bound with fastening means such as a cord 50.

On the other hand, a plug 52 made of, for example, a metal is provided in front of the connector 44. The plug 52 is linked with the connector 44 by a second linking tube 54 made of a flexible plastic which constitutes second linking means. The second linking tube 54 is secured at the opposite ends thereof to the shoe 52 and the connector 44 by being bound with codes 56. The linking tube 54 is formed with a through-hole 54A.

In the embodiment, a tube which constitutes the first balloon 1 extends forward to the plug 52 through the connector 44 to provide the second balloon 2. In another embodiment of the present invention, the first balloon 1 may be separated from the second balloon 2. The front end portion of the second balloon 2 is secured to the plug 52 by being bound with fastening means such as code 58. The first and second balloons 1 and 2 are made of an expandable material having a flexibility and an elasticity. They are made of rubber latex in the embodiment and may be made of silicone rubber.

The plug 52 includes a semi-spherical portion 52A at the front end thereof, a cylindrical portion at the intermediate position and a small diameter portion at the rear end thereof. The semi-spherical portion 52A is formed with main urination opening 52B and subsidiary urination openings 52C which open at the center and both sides of the portion 52A and are communicated with a common urination tube 52D which opens at the rear end of the small diameter portion.

The urination tube 18 which is fitted into the small diameter portion of the plug 52 extends through the connector 44 and passes through the second guide 14 and opens externally as shown in FIG. 1. Accordingly, when urination occurs during an surgical operation, urine flows into any of the urination openings and is externally discharged via the urination tubes 52D and 18. Such urination means provides a very effective means since heating of the prostate promotes urination in a prostate operation. The reason why the urination openings are provided at the center and on both sides of the semi-spherical portion 52A is to smoothly discharge urine via the openings if any of the openings is clogged with the bladder.

On the other hand, the second balloon inflating coolant supply tube line 20 extends into the second guide 14 and extends through the connector 44 and enters the second linking tube 54. The cooling water W2 which is externally supplied flows through the second balloon inflating coolant supply tube line 20 and supplied into the second linking tube 54 and then introduced into the second balloon 2 via the communicating hole 54A for inflating the second balloon 2. The second balloon 2 is deflated by draining the cooling water W2 via the second balloon inflating coolant supply tube line 20.

As shown in FIG. 2, the lead line 16 of the temperature sensor extends through a space between the first and second guides 12 and 14 and around the outer periphery of the connector 44 and then extends through the second guide 14 and is in contact with the inner surface of the first balloon 1 in the intermediate position along the length thereof. The front end of the lead line 16 is sandwiched between reflecting strips made of two aluminum foils and plastic sheets containing white pigment for reflecting lights. The reflecting strips 16A are bonded to the inner surface of the first balloon 1 with a boding agent.

The laser balloon catheter may be preferably used for the treatment of the prostate. When the cooling water W1 and W2 is not pumped at a pressure, the first and second balloons 1 and 2 are deflated by their own deflating power. At this time, the second guide 14 is also deflated in association with the deflation of the first balloon 1.

Figure 5:
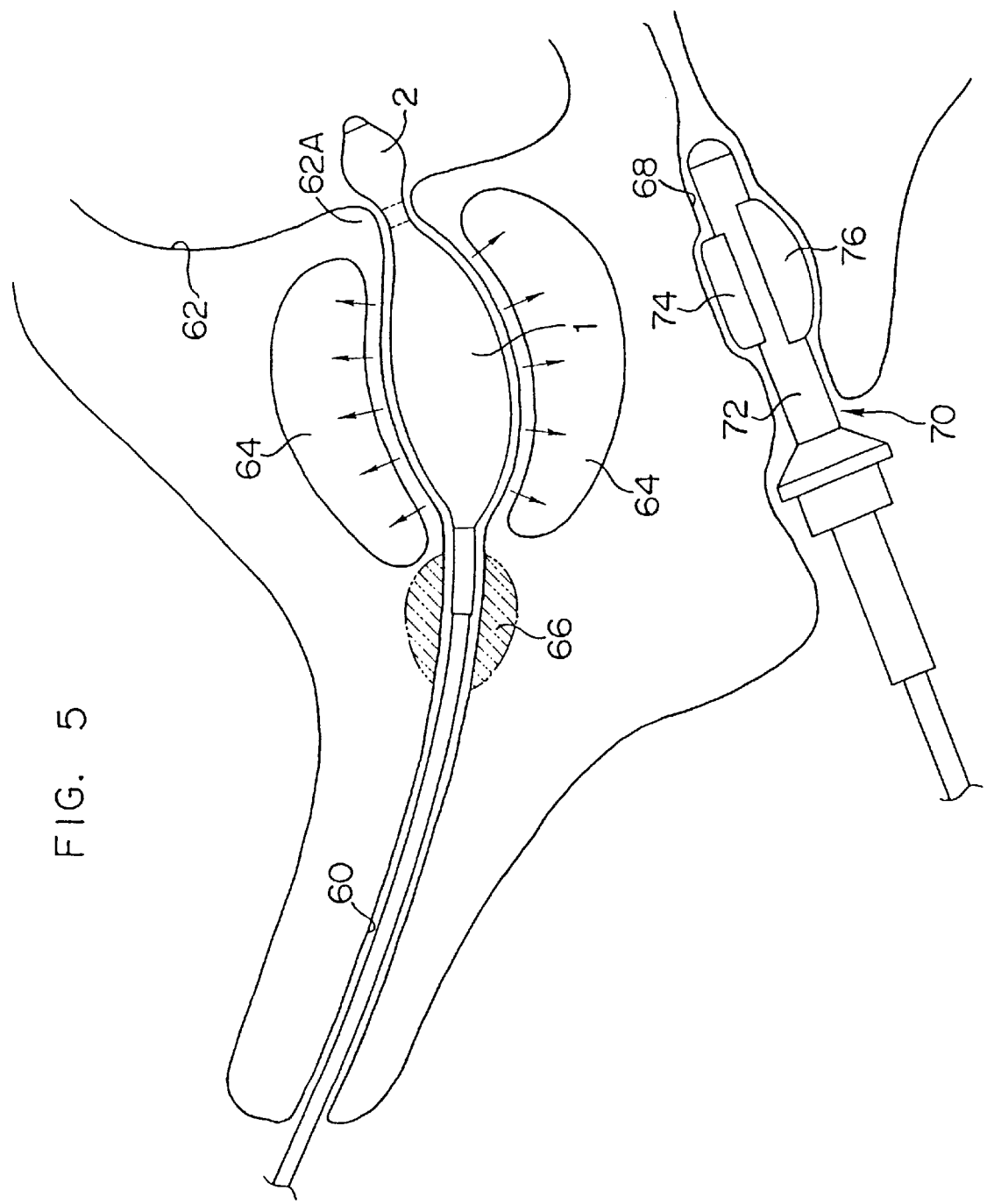
FIG. 5 is an explanatory view showing the treatment of the prostate.

In this condition, the laser balloon catheter is inserted into the urethra 60 to position the second balloon 2 in the bladder 62 as shown in FIG. 5. Then, the cooling water W1 is supplied to the inflatable portion 14A of the second guide 14 from the cooling water tank 28 by the circulating pump 30 via the tube 32 and a space between the first and second guides 12 and 14 for inflating the inflatable portion 14A. This inflation causes the first balloon 1 to be also inflated as shown in FIGS. 2 and 5. The cooling water W1 used for inflation flows into the first guide 12 via the discharge tube 52 and is returned to the cooling water tank 28 via the communicating hole 46 and tube 34.

The cooling water W2 is also supplied to the second balloon 2 via the second balloon inflating coolant supply tube line 20, the second linking tube 54 and then the communicating hole 54A for inflating the second balloon 2 as shown in FIGS. 2 and 5.

Laser lights from the laser light generator 26 are incident upon the optical fiber 38 via the connector 36 and are emitted from the core 38A at the front end of the optical fiber 38. The laser lights incident upon the protection tube 40 or the first liking tube 46 of the emitted laser lights are transmitted directly through the tubes 40 and 46 or transmitted therethrough after repeating reflection and diffusion and are ultimately diffused in a lateral direction and are incident upon the prostate 84 via the second guide 14 and the first balloon 1. If some of the forward travelling laser lights are incident upon the gold plated coil spring 48 while travelling in a forward direction, they are reflected by the coil spring 48 and are diffused in a lateral direction and are incident upon the prostate 64 via the first linking tube 46, the second guide 14 and the first balloon 1.

The laser lights which travel forwardly without colliding with the coil spring 48 are reflected on the gold plated layer 44B and some of them are reflected in a lateral direction while they travel rearward or they are collided with the coil spring 48. The reflected lights travelling rearward are reflected upon the gold plated front surface of the circular portion 42A of the holder 42 and will then travel forward. In such a manner, the laser lights are diffused in a lateral direction after repeating the reflections. Therefore, the laser lights are emitted toward the prostate from the entire surface of the first balloon 1 at a higher amount of light in the central position along the length of the balloon and at a lower amount of light at the opposite ends of the balloon 1.

The laser lights which are incident upon the prostate 64 are absorbed by the tissue in the prostate 64 to generate heat. As a result, the prostate 64 is warmed or heated. Heating with the laser lights are maintained for a given period of time. The diseased tissue in the prostate 64 is thus heated on exposure to laser lights to necroses and the other tissue of the prostate will recover soon after operation. The laser lights will be well absorbed by the protein in the tissue particularly when Nd—YAG laser lights are used.

Heating of the prostate with ultrasonic waves is possible. Although many of the ultrasonic waves are absorbed by the water content in the tissue of the prostate, the percent of the ultrasonic waves absorbed by the tissue is lower and the curing effect is low. In contrast to this, the ratio of the laser lights, in particular, Nd—YAG laser lights absorbed by the water content is about 10% and the rest of the laser lights is absorbed by the protein in the tissue.

In the embodiment of the present invention, the inside of the first balloon 1 is cooled by the cooling water W1 forcedly circulated through the second guide 14 to keep it at a given temperature. When the forced cooling is not conducted, the power of the laser lights decreases as they travel from the inner wall of the urethra to the deeper portion of the prostate. The inner wall of the urethra is heated to a higher temperature while the deeper portion of the prostate is heated to the lower temperature as represented by the temperature distribution curve Y in FIG. 6.

If the power of the laser lights is increased to heat the tissue from the inner wall of the urethra to the center of the prostate which is about 6 to 12 mm deep therefrom, the inner wall of the urethra and the tissue in the vicinity thereof is excessively heated and may be damaged. It becomes more difficult to cure the damaged tissue.

Figure 6:
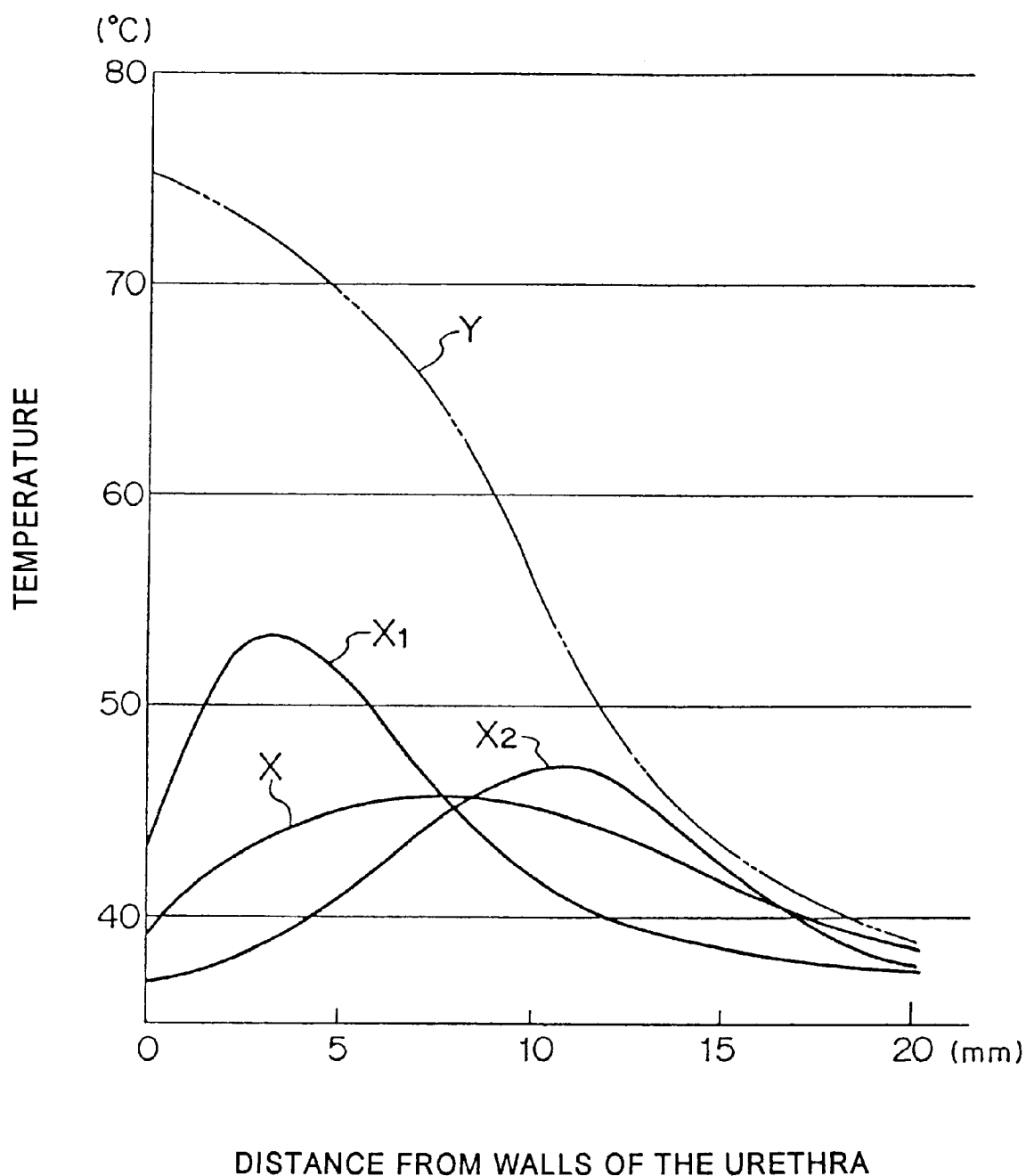
FIG. 6 is a graph showing the distribution of the temperature from the inner wall of the urethra in a depth direction when forced cooling is conducted and not conducted.

When the inside of first balloon 1 and the inflatable portion 14A of the second guide 14 is cooled with the cooling water W1, the tissue in the vicinity of the urethra is cooled as represented by the temperature distribution curve X in FIG. 6 to prevent it from damaging while the laser lights are incident upon the central portion of the prostate at an enough amount so that the tissue to the central portion is positively heated. In this case, the temperature distribution can be adjusted as represented by the temperature distribution curve X1 or X2 in FIG. 6 by controlling the power of the laser lights and the circulating amount or the temperature of the cooling water W1. Curing effect can be enhanced by adjusting the temperature distribution depending upon the symptoms of the prostate.

For the prostatitis, the inside of the prostate is heated at a temperature not high than 43° C. by forcedly cooling it with the cooling water W1. For the prostatomegaly, the inside of the prostate is heated to 45° C. or higher for necrotization while the inner wall of the urethra and the tissue in the vicinity thereof is protected from the thermal damage by forcedly cooling it with the cooling water W1. The necrosed tissue is metabolically absorbed to reduce the size of the prostate to open the urethra.

The lengths of the balloon 1 and the inflatable portion 14A of the second guide 14 or the position of the front end of the optical fiber 38 is preset in such a manner that the laser lights are prevented from impinging upon the sphincter muscle 66.

The second balloon 2 is effective primarily to position the laser balloon catheter and secondarily to prevent the laser balloon catheter from removing from the bladder 62 during operation. That is, the first balloon 1 is positioned in a position corresponding to the prostate by inflating the second balloon 2 and then removing the laser catheter until the second balloon 2 abuts upon the neck portion 62A of the bladder 62 after the laser balloon catheter has been inserted to locate the second balloon 2 in the bladder 62. After completion of this positioning, the first balloon 1 is inflated. Even if the laser balloon catheter is shifted during operation, the laser balloon catheter can be prevented from removing from the bladder 62 since the second balloon 2 would abut on the neck portion 62A of the bladder 82.

The temperature of the inner wall of the urethra is detected by a thermocouple which is provided at the front end of the lead line 16. A signal representing the temperature is input to a temperature control unit 24 via the lead line 16 and the connector 22. The temperature of the inner wall of the urethra is controlled by adjusting the interval of the turn on or off time of the laser light generator 26 depending upon the difference between the detected temperature and a target temperature of the inner wall of the urethra. Control of the temperature of the center of the prostate is possible by preliminarily determining the correlation between the temperature of the center of the prostate and the temperature of the inner wall of the urethra.

Since excessive penetration of the laser lights into the prostate to heat it will cause the tissue of the prostate to be damaged, it is preferable to insert a temperature detecting probe 70 into the rectum 68 as shown in FIG. 5. The temperature detecting probe 70 comprises a temperature sensor 74 having a plurality of, for example, 5 thermocouples disposed at the front end of a metal tube having a high rigidity on one side thereof so that the front ends of the thermocouples face externally and a balloon 76 on the other side for biasing the sensor 74. The lead lines for respective thermocouples of the temperature sensor 74 are electrically connected to an external device such as the temperature control unit 24. The biasing balloon 76 is inflated by an external pressure source such as air source after the temperature detecting probe 70 has been inserted into the rectum 68. The inflated balloon 76 will bias the temperature detecting probe toward the rectum 68 and to closely contact with the inner wall of the rectum 68.

Irradiation of the prostate 64 with laser lights causes the prostate to be warmed or heated. Some of the laser lights are transmitted through the prostate 64 to reach the side of the rectum 68 so that the tissue in the vicinity of the rectum 68 is also heated. If the temperature of the inner wall of the rectum 68 which is detected by the temperature sensor 74 exceeds a preset temperature, the turn-off period of time of the laser light generator 26 is extended or the power of the laser lights is lowered to prevent excessive heating of the prostate 64. Thermal damage on the rectum 68 can be also prevented.

Figure 7:
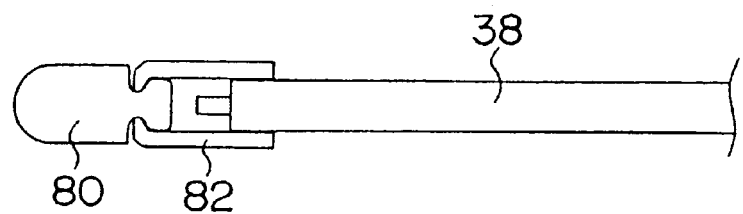
FIG. 7 is a longitudinal sectional view showing an embodiment in which a chip is used as a laser emitting end.

The present invention includes a further embodiment which is illustrated in FIG. 7. The optical fiber is not provided as means for emitting laser lights. A chip 80 through which the laser lights are transmitted is provided in front of the optical fibers 38. The laser lights from the front end of the optical fibers 38 are incident upon the chip 80 so that the laser lights are ultimately emitted from the chip 80. The optical fibers are linked with the chip by an appropriate linking fitting 82.

In a further embodiment, the inflating portion 14A of the second guide 14 does not extend to the connector 44 through the first balloon 1 and is terminated slightly in front of a code 84 for fastening the first balloon 1 of FIG. 2 to the second guide 14 so that the first balloon 1 is inflated directly by pumping the cooling water W1.

A double film structure of the first balloon 1 and the second guide 14 in which the inflatable portion 14A of the second guide 14 extends to the connector through the first balloon 1 provides various advantages. If the first balloon 1 is made of rubber latex, the inflated first balloon 1 will become semispherical in shape, and is difficult to become elliptical In longitudinal section. Accordingly, a plastic tube is preliminarily provided and the plastic tube is pressurized and heated at the front end portion thereof for blow working to form the inflating portion 14A having the same and large diameter. When the inflating portion 14A is inflated, it will not be inflated beyond the preliminarily fabricated shape. As a result, the shape of the inflated first balloon 1 will follow the shape of the inflatable portion 14A. A second advantage is that the front end of the lead line 16 is adhered to the inner surface of the first balloon 1 by the introduction of the lead line 16 between the first balloon 1 and the inflated portion 14A to prevent an error in detected temperature from occurring when the inflating portion 14A is inflated even if the front end of the lead line 14 should be separated from the inner surface of the first balloon. A third advantage is that leakage of water is prevented by the double film structure even if one of the films is torn. The inflatable portion 14A of the second guide 14 is automatically deflated by the deflating power of the first balloon 1 if the cooling water introduced to the inflatable portion 14A is drained.

Although the cooling water W1 flows through a space between the first and second guides 12 and 14 and flows into the first guide 12 through the communication hole 46 and is discharged through a space in the first guide 12 in the above mentioned embodiment, the direction of the flow of the cooling water may be reversed.

The reason why the first linking tube 46 is provided separately from the first guide 12 is to make easier the assembling such as setting of the holder 42 and the protection tube 40 on the front end portion of the first guide 12 and setting of the spring 48 within the first linking tube 46. Accordingly, the first linking tube 48 may be omitted and the first guide 12 may extend to fit into the small diameter portion 44A. In this case, the first guide 12 is formed with a communication hole for the cooling water W1.

Although Nd—YAG laser lights are most preferable as laser lights as mentioned above, argon laser or diode laser lights and the like may be used. Since the laser lights are absorbed by water at a very low percentage, they are transmitted through the cooling water and are impinged upon the tissue at an enough rate.

Although cooling water is used for inflating the first and second balloons 1 and 2, air, nitrogen gas and carbon oxide gas and the like may be used. Other cooling liquid such as alcohol may be used.

In order to smoothly insert the laser balloon catheter of the present invention into the tissue, it is preferable that the first and second guides 12 and 14 and the first and second linking tubes 16 and 54 be flexible. If it suffices to insert the catheter rectlinearly, at least one of these components may be nonflexible.

Figure 8:
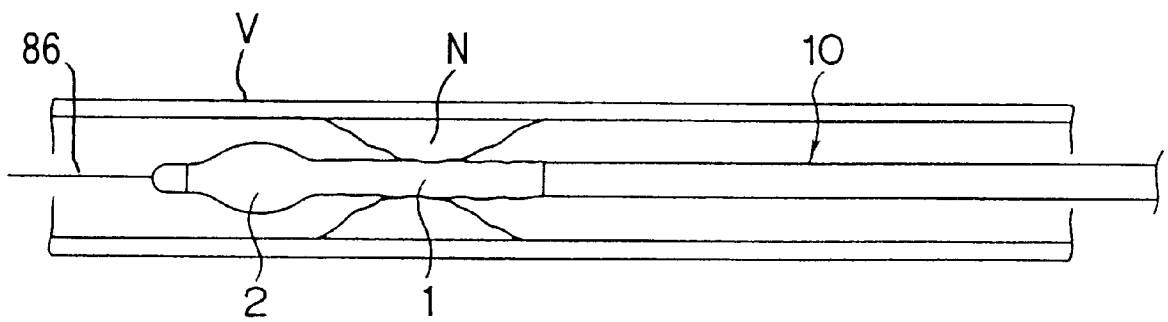
FIG. 8 is a schematic view showing the manner in which the laser balloon catheter is inserted into the stricture of the blood vessel.
Figure 9:
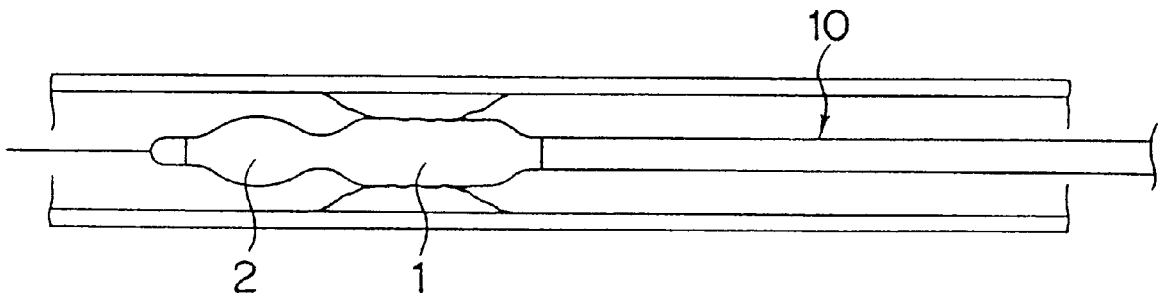
FIG. 9 is a schematic view showing the manner in which the stricture of the blood vessel is irradiated with the laser lights.

The laser balloon catheter of the present invention is also effective for the treatment of the other tissues. For example, the catheter is effective for expanding a stricture N of the blood vessel V as shown in FIG. 8. In this case, a guide wire 86 is preliminarily inserted into the urination tube 18. After or while the guide wire 86 is inserted into the target blood vessel V, the laser balloon catheter is inserted into the vessel V. Subsequently, the second balloon 2 is inflated as shown in FIG. 9. Thereafter, the laser balloon catheter is removed. When the shoulder at the rear end of the second balloon 2 abuts on the stricture N, a surgical operator recognizes the presence of the stricture N in rear of the second balloon 2 by the hand's feeling. While the first balloon 1 is inflated in this position, the stricture N is irradiated with the laser lights to be vaporized for expanding the vessel.

Figure 10:
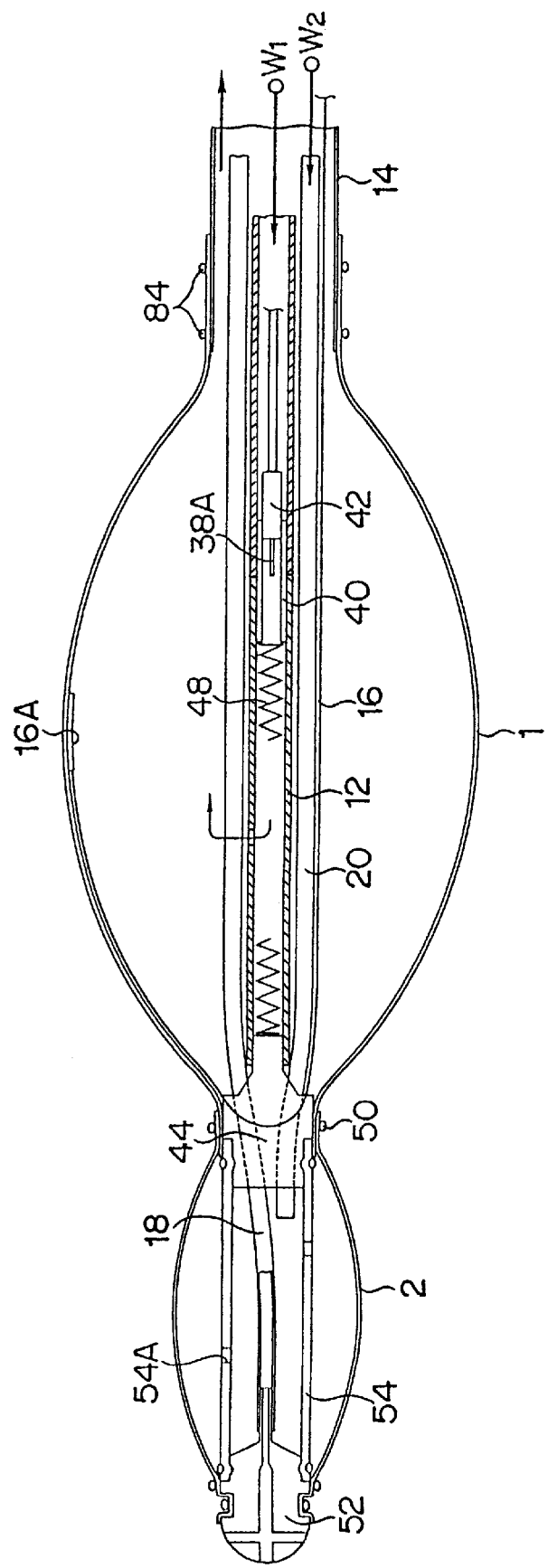
FIG. 10 is a longitudinal sectional view showing the structure of an another laser balloon catheter.

FIG. 10 shows a further embodiment in which the first balloon 1 is provided separately from the second balloon 2, the second guide 14 does not extend forward, the first balloon 1 is not a double film structure but a single structure and the first guide 12 extends to fit into the small diameter portion 44A. In this embodiment, the first guide 12 constitutes the first liking means.

Since the second balloon is provided in front of the first balloon in the present invention as mentioned above, the laser balloon catheter can be positioned in position.

In the treatment of the prostate, the laser balloon catheter can be prevented from removing during the operation. Furthermore, when urination occurs during the operation, the urine can be smoothly discharged to the outside of the body.

What is claimed is:

1. A laser balloon catheter for irradiating a tissue with laser light, comprising:

laser light emitting means including an optical fiber having a laser light receiving end and a laser light emitting end;

a first inflatable balloon having front and base ends, said first inflatable balloon provided around said laser light emitting means for transmitting laser light emitted from the laser light emitting means via a wall of the first balloon to the tissue with the first balloon inflated and in direct pressing contact with the tissue;

a first fluid passage within said first inflatable balloon for supplying a first cooling fluid into said first balloon to inflate the first balloon and for discharging said first cooling fluid to deflate the first balloon;

a second inflatable balloon of smaller size than said first inflatable balloon, said second inflatable balloon having front and base ends with the base end thereof connected to said front end of said first balloon, a narrow neck portion being formed at the connection between the first and second balloons;

a second fluid passage within said second inflatable balloon for supplying a second fluid into said second balloon to inflate the second balloon and for discharging said second fluid to deflate the second balloon;

a plug secured to said front end of said second balloon, said plug having an orifice for receiving bodily fluids;

a tube communicating with said orifice for externally discharging said bodily fluids;

a first guide means for surrounding and guiding said optical fiber; and a second, flexible guide means provided around said first guide means for providing a space accommodating a conduit for fluid flow to said second balloon, said second, flexible guide means comprising a pre-inflated front end portion within said first inflatable balloon, said pre-inflated front end portion of said second, flexible guide means receiving said first cooling fluid supplied by said first fluid passage for inflating said first inflatable balloon, wherein a base end portion of said first balloon is secured to said second guide means, said first fluid passage being formed between said first and second guide means.

2. The laser balloon catheter according to claim 1, further comprising:

connecting means having front and base ends, said front end of said connecting means secured to said front end of said first balloon and said base end of said connecting means secured to said base end of said second balloon; and flexible laser light transmitting linking means for linking said connecting means with said guide means.

3. A laser balloon catheter for irradiating tissue with laser light comprising:

laser light emitting means including an optical fiber having a laser light receiving end and a laser light emitting end;

a first inflatable balloon having front and base ends, said first inflatable balloon provided around said light emitting means for transmitting the laser light emitting means via a wall of the first balloon to the tissue with the first balloon inflated and in direct pressing contact with the tissue;

first fluid passage within said first inflatable balloon for supplying a first cooling fluid from a first fluid supply means into said first balloon to inflate the first balloon and for discharging said first fluid to deflate the first balloon;

a second inflatable balloon of smaller size than said first inflatable balloon; said second inflatable balloon having front and base ends with the base end thereof connected to said front end of said first balloon, a narrow neck portion being formed at the connection between the first and second balloons;

a second fluid passage within said second inflatable balloon for supplying a second fluid into said second balloon to inflate the second balloon and for discharging said second fluid to deflate the second balloon;

connecting means having front and base ends, said front end of said connecting means secured to said front end of said first balloon and said base end of said connecting means secured to said base end of said second balloon;

first guide means surrounding and guiding said optical fiber;

second flexible guide means surrounding said first guide means for providing a space accommodating a conduit for fluid flow to said second balloon, said second, flexible guide means comprising a pre-inflated front end portion within said first, inflatable balloon, said pre-inflated front end portion of said second, flexible guide means receiving said first cooling fluid supplied by said first fluid passage for inflating said first inflatable balloon, a first flexible and laser light transmittable linking means for linking said connecting means with said first guide means;

a plug secured to said front end of said second balloon, said plug having an orifice for receiving bodily fluids;

a tube communicating with said orifice for externally discharging said bodily fluids;

second linking means comprising a front end and a base end for linking said plug with said connecting means; and the second balloon being secured to said connecting means at the base end thereof.

4. A laser balloon catheter according to claim 3, wherein said first linking means is tubular and is in fluid communication with said first guide means through said first fluid passage.

5. A laser balloon catheter according to claim 3, in which said second linking means is tubular and is in fluid communication with a second fluid supply source via said second fluid passage and said connecting means.

6. A laser balloon catheter according to claim 3, wherein said plug contains a hole extending therethrough, and wherein said hole communicates with the orifice and with a discharge passage leading outside of the catheter.

7. A laser balloon catheter according to claim 3, wherein said plug contains a hole which opens externally at said orifice; and said second linking means contains a discharge passage in communication with said hole for discharging fluid outside of the catheter via said first balloon.

8. A laser balloon catheter according to claim 3, wherein said second fluid passage extends between said first and second guide means.

9. A laser balloon catheter according to claim 3, further comprising a discharge passage extending between said first and second guide means.

10. A laser balloon catheter according to claim 3, wherein said plug comprises a front end and a rear end, a hemispherical portion at the front end thereof, a cylindrical portion at an intermediate position and a small diameter portion at the rear end thereof.

11. The laser balloon catheter according to claim 10, wherein said hemispherical portion comprises a plurality of orifices.

12. The laser balloon catheter according to claim 11, wherein said hemispherical portion comprises a main orifice in a central portion thereof and an orifice at each side of said central orifice, which orifices communicate with a common urination tube which opens at the small diameter portion.

13. The laser balloon catheter according to claim 12, wherein the urination tube extends through said connecting means, passes through said first guide means and opens externally.

* * * * *